Figure 1:
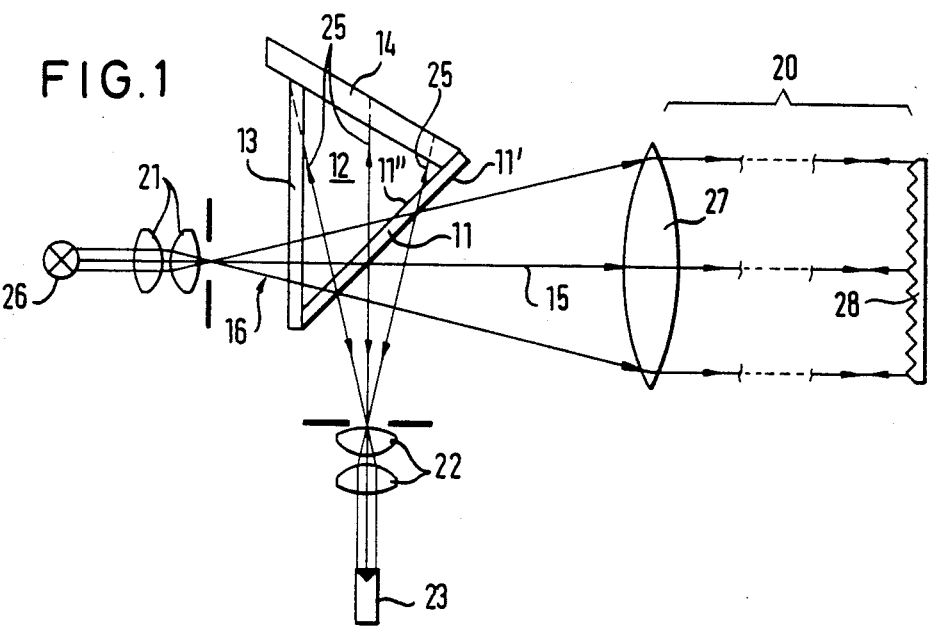

United States Patent [19]

Smetana

[11] Patent Number: 4,561,722
[45] Date of Patent: Dec. 31, 1985

[54] BEAM DIVIDER
[75] Inventor: Klaus Smetana, Grünwald, Fed. Rep. of Germany
[73] Assignee: Erwin Sick GmbH Optik-Elektronik, Waldkirch, Fed. Rep. of Germany
[21] Appl. No.: 522,300
[22] Filed: Aug. 11, 1983
[30] Foreign Application Priority Data Aug. 23, 1982 [DE] Fed. Rep. of Germany ........ 3231265

[51] Int. Cl.⁴ ..................... G02B 27/14; G01N 21/59
[52] U.S. Cl. .................................. 350/171; 250/574; 356/438; 350/590
[58] Field of Search ............... 350/171, 169, 174, 291, 350/164, 590; 356/438, 437; 250/574

[56] References Cited

U.S. PATENT DOCUMENTS

| 2,369,741 | 2/1945 | Jones et al. | 350/164 |
| 3,198,097 | 8/1965 | Hine | 350/171 |
| 3,772,507 | 11/1973 | Hills | 350/171 |
| 3,944,336 | 3/1976 | Carr | 350/291 |

OTHER PUBLICATIONS

Soller et al., *Cathode Ray Tube Displays*, M.I.T. Radiation Labs., vol. 22, pp. 564–569, 1948.

*Primary Examiner*—Jon W. Henry
*Attorney, Agent, or Firm*—Townsend & Townsend

[57] ABSTRACT

A beam divider which is particularly intended for use in smoke measuring apparatus comprises a transparent beam dividing plate (11) which is obliquely arranged in the beam path and is partially silvered at its lower side (11'). Two protective plates (13, 14) which form a closed internal space (12) leave the upper side of the beam dividing plate (11) above and below the optically active region. At least the protective plate (13) which crosses the beam path is transparent and the arrangement is closed in a dust-tight manner at the end faces.

10 Claims, 4 Drawing Figures

BEAM DIVIDER

The invention relates to a beam divider comprising a transparent beam dividing plate which is obliquely arranged in the beam path and is partially reflective at its lower side.

With beam dividers, in particular for smoke density measuring apparatus, a film frequently forms on the upper side of the physical beam dividing plate, which is preferably arranged at 45° to the beam path or optical axis. This film falsifies the measurement result which makes itself noticeable by a drift of the calculated output value.

The object of the present invention is to reduce or entirely to avoid this film formation.

In order to satisfy this object the invention envisages an arrangement in which first and second protective plates which form a closed internal space leave the upper side of the beam dividing plate above and below the optically active region, with at least the first protective plate which crosses the beam path being transparent and with the arrangement being enclosed in a dust-tight manner at the end faces.

In particular the arrangement should be such that the first protective plate extends from the lower edge region of the beam divider plate substantially at right angles to the optical axis through the beam path, and such that the upper edge region of the beam divider plate and the first protective plate are connected by the second protective plate, which is preferably constructed as an optical sink.

In this manner the upper side of the beam divider plate can be fully closed from the outside so that a film can no longer form there. The film formation on the preferably partly transmitting, reflectively coated, lower side can be ignored.

Film formation on the flat glass of the first protective plate which extends at right angles to the optical axis is not disturbing because this lies outside of the field of view of the photoreceiver and does not therefore contribute to the drift.

The second upper protective plate should form an optical sink in order to transmit, to absorb or to render harmless by reflection the transmitted light which is deflected thereto. The second, upper, protective plate is for this reason expediently obliquely arranged relative to the optical axis.

Whereas the first protective plate is expediently bloomed (rendered anti-reflective) on both sides, the second protective plate and the beam divider plate should preferably only be bloomed at the inner side.

In order to securely mount the beam divider of the invention a holding block should be secured to one or both end walls.

Figures 3, 4:
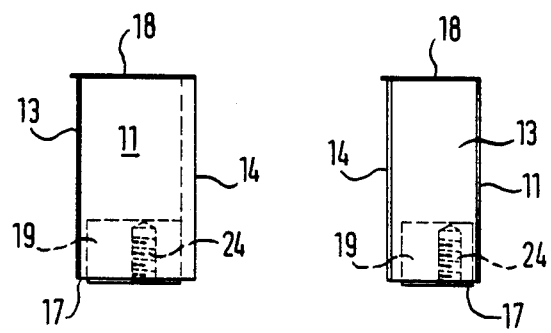
Figure 2:
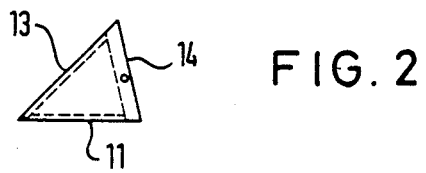

The invention will now be described in the following with reference to the drawings in which is shown:

FIG. 1: a schematic side view of a beam divider in accordance with the invention, with the beam divider being arranged in the optical beam path of a smoke density measuring apparatus, FIG. 2: an end view of a constructional realisation of the beam divider of the invention, and FIGS. 3 and 4: further views of the beam divider of FIG. 2.

As seen in FIG. 1 a light beam 16 is directed along a beam path or measurement path 20 by a schematically arranged light source 26 via a condenser 21. A beam divider plate 11 is arranged in the light beam 16 at an angle of 45° to the optical axis 15 and is provided at its lower side with a partially transmitting mirror layer 11'. The upper side is bloomed, i.e. rendered non-reflective.

Beneath the beam divider plate 11 there is located a lens pair 22 by means of which light reflected via the beam divider plate 11 out of the measurement path 20 in a downward direction is concentrated on a photoreceiver 23.

In accordance with the invention a first plane parallel transparent protective plate 13 which is arranged at right angles to the optical axis 15 extends from the lower edge of the beam divider plate 11 vertically upwardly. A second light absorbing protective plate 14 extends at an angle of 67.5° from the upper edge of the beam divider plate 11 to the upper edge of the first protective plate 13. The three plates 11, 13, 14 are connected together at their edges in a dust-tight manner so that a closed inner space 12 is formed.

As seen in FIGS. 2 and 4 the end faces of the inner space 12 are also closed in dust-tight manner by the end walls 17, 18. The lower end wall 17 as seen in FIGS. 3 and 4 is formed by a holder block 19 which partly projects into the inner space 12. An outwardly opening threaded bore 24 is provided in the holder block by means of which the beam divider can be secured in a suitable manner.

The upper side 11" of the beam divider plate 11 which is sensitive to contamination is thus effectively protected against external influences. The transmitted light which is reflected upwardly from the beam divider plate and indicated by the reference numeral 25 is either transmitted, absorbed or so reflected by the protected plate 14 that it can no longer reach the receiver 23.

It will be appreciated that the light beam 16 passes from the source 26 as a diverging beam through the beam divider plate 11 a lens 27 on the other side of the beam divider plate 11 converts the beam into a parallel beam which falls on a retroreflector 28 at the other side of the measurement path 20. The measurement path may, for example, extend across a smoke stack. Light reflected from the retroreflector is passed back to the beam divider plate 11 and reflected downwardly to the detector 23.

I claim:

1. In apparatus for measuring optical transmissivity along a measuring path, said apparatus including light transmitting means for transmitting a beam of light along said measuring path, a retroreflector disposed at an end of said measuring path for retroflecting said beam back along said measuring path, and light receiving means for receiving the retroreflected beam, a beam divider comprising a beam dividing plate having spaced apart lower and upper edges and being set at an oblique angle to said beam of light from said light transmitting means so as to pass said beam along said measuring path and to deflect the retroreflected beam downward therefrom to said light receiving means positioned therebelow; a first protective transparent plate extending upward from said lower edge through said beam of light and substantially perpendicular thereto; a second protective plate extending from said upper edge to said first protective plate at a position on the opposite side of said beam of light from said lower edge; and wall means interconnecting said first and second protective plates and said beam divider to define a closed internal space therebetween.

2. A beam divider in accordance with claim 1, wherein a surface of at least one of said first and second protective plates facing inward toward said closed internal space is rendered nonreflective.

3. A beam divider in accordance with claim 2, wherein the surfaces of both said first and second protective plates facing inward toward said closed internal space are rendered nonreflective.

4. A beam divider in accordance with claim 2, wherein the surfaces of said beam dividing plate facing inward toward said closed internal space is rendered nonreflective so as to minimize the portion of said beam deflected upward therefrom.

5. Apparatus for measuring the optical transmissivity along a measuring path extending between a light transmitting and receiving arrangement and a retroreflector, said light transmitting and receiving arrangement comprising a light source disposed to provide a beam of light along the direction of said measuring path, a beam dividing plate having spaced apart first and second edges, means mounting said beam dividing plate at an oblique angle to said measuring path so that said beam of light falls on said beam dividing plate between said edges, a first protective transparent plate extending from said first edge through said beam of light and substantially perpendicular thereto, a second protective plate extending from said second edge to said first protective plate at a position on the opposite side of said beam of light from said first edge, wall means interconnecting said first and second protective plates and said beam divider to define a closed internal space therebetween, and a photoreceiver disposed on the opposite side of said beam dividing plate from said first and second protective plates to receive light via said beam dividing plate reflected by said retroreflector.

6. Apparatus in accordance with claim 5, wherein said beam dividing plate has inner and outer sides relative to said closed internal space, with said inner side being rendered nonreflective and with said outer side being partially reflective.

7. Apparatus in accordance with claim 5, wherein said second protective plate is obliquely arranged relative to said measuring path and is diposed at an upper end of said beam divider.

8. Apparatus in accordance with claim 5, wherein said first protective plate has inner and outer sides relative to said internal space and is rendered nonreflective on said sides.

9. Apparatus in accordance with claim 5, wherein said second protective plate has inner and outer sides relative to said internal space and wherein said inner side is rendered nonreflective.

10. Apparatus in accordance with claim 5, wherein said wall means comprises first and second end walls and said apparatus further comprises a mounting block secured to at least one of said end walls.

* * * * *